US011278551B2

(12) United States Patent
Smith et al.

(10) Patent No.: US 11,278,551 B2
(45) Date of Patent: Mar. 22, 2022

(54) TREATING CANCER WITH A CCK RECEPTOR INHIBITOR AND AN IMMUNE CHECKPOINT INHIBITOR

(71) Applicant: GEORGETOWN UNIVERSITY, Washington, DC (US)

(72) Inventors: Jill P. Smith, Camp Hill, PA (US); Louis Weiner, Washington, DC (US); Sandra Jablonski, Silver Spring, MD (US); Sandeep Nadella, Alexandria, VA (US); Shangzi Wang, Derwood, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 100 days.

(21) Appl. No.: 16/493,882

(22) PCT Filed: Mar. 15, 2018

(86) PCT No.: PCT/US2018/022617
§ 371 (c)(1),
(2) Date: Sep. 13, 2019

(87) PCT Pub. No.: WO2018/170254
PCT Pub. Date: Sep. 20, 2018

(65) Prior Publication Data
US 2020/0383996 A1    Dec. 10, 2020

Related U.S. Application Data

(60) Provisional application No. 62/471,761, filed on Mar. 15, 2017.

(51) Int. Cl.
*A61K 31/5513*    (2006.01)
*A61P 35/00*    (2006.01)
*A61K 31/198*    (2006.01)
*C07K 16/28*    (2006.01)

(52) U.S. Cl.
CPC ........ *A61K 31/5513* (2013.01); *A61K 31/198* (2013.01); *A61P 35/00* (2018.01); *C07K 16/2818* (2013.01)

(58) Field of Classification Search
CPC .. A61K 31/197; A61K 31/5513; C07K 16/28; C07D 233/35; C07D 403/12
USPC .................... 514/221, 563; 540/509; 562/400
See application file for complete search history.

(56) References Cited

U.S. PATENT DOCUMENTS

2003/0091574 A1    5/2003    Gevas et al.
2016/0361298 A1    12/2016    Novick et al.
2017/0056347 A1    3/2017    Glick et al.

OTHER PUBLICATIONS

Abbruzzese et al., "A Pilot Clinical Trial of The Cholecystokinin Receptor Antagonist MK-329 In Patients With Advanced Pancreatic Cancer", Pancreas, vol. 7, 1992, pp. 165-171.
Abu Eid et al., "Old-School Chemotherapy in Immunotherapeutic Combination in Cancer, A Low-cost Drug Repurposed", Cancer Immunology Research, vol. 4, No. 5, May 2016, pp. 377-383.
Amedei et al., "Pancreatic Cancer: Role of The Immune System in Cancer Progression and Vaccine-based Immunotherapy", Human Vaccines & Immunotherapeutics, vol. 10, No. 11, Nov. 2014, pp. 3354-3368.
Apte et al., "A Starring Role for Stellate Cells in the Pancreatic Cancer Microenvironment", Gastroenterology, vol. 144, No. 6, Jun. 2013, pp. 1210-1219.
Apte et al., "Desmoplastic Reaction in Pancreatic Cancer: Role of Pancreatic Stellate Cells", Pancreas, vol. 29, 2004, pp. 179-187.
Bardram et al., "Progastrin Expression in Mammalian Pancreas", Proceedings of the National Academy of Sciences of the United States of America, vol. 87, Jan. 1990, pp. 298-302.
Benedetti et al., "The Biochemical and Neuroendocrine Bases of the Hyperalgesic Nocebo Effect", The Journal of Neuroscience, vol. 26, No. 46, Nov. 15, 2006, pp. 12014-12022.
Berna et al., "CCK1 and CCK2 Receptors Are Expressed on Pancreatic Stellate Cells and Induce Collagen Production", The Journal of Biological Chemistry vol. 285, No. 50, Dec. 10, 2010, pp. 38905-38914.
Berna et al. , "Role of CCK/Gastrin Receptors in Gastrointestinal/ Metabolic Diseases and Results of Human Studies using Gastrin/ CCK Receptor Agonists/Antagonists in these Diseases", Current Topics in Medicinal Chemistry, vol. 7, No. 12, 2007, pp. 1211-1231.
Boj et al., "Organoid Models of Human and Mouse Ductal Pancreatic Cancer", Cell, vol. 160, No. 0, Jan. 2015, pp. 324-338.
Brand et al., "Differential Gastrin Gene Expression in Rat Gastrointestinal Tract and Pancreas During Neonatal Development", The Journal Of Biological Chemistry, vol. 263, No. 11, Apr. 15, 1988, pp. 5341-5347.
Carriere et al., "Acute Pancreatitis Markedly Accelerates Pancreatic Cancer Progression in Mice Expressing Oncogenic Kras", Biochemical and Biophysical Research Communications, vol. 382, No. 3, May 8, 2009, pp. 561-565.

(Continued)

*Primary Examiner* — Jeffrey H Murray
(74) *Attorney, Agent, or Firm* — Kilpatrick Townsend & Stockton LLP

(57) ABSTRACT

Provided herein are methods for treating a cholecystokinin (CCK) receptor-expressing cancerous tumor in a subject. The methods comprising administering to the subject an effective amount of a CCK receptor inhibitor and an effective amount of an immune checkpoint inhibitor, wherein the CCK receptor inhibitor inhibits one or more CCK receptors selected from the group consisting of a CCK-A receptor, a CCK-B receptor and a CCK-C receptor, and wherein the immune checkpoint inhibitor is a programmed cell death protein 1 (PD1) inhibitor or a cytotoxic T-lymphocyte-associated antigen 4 (CTLA-4) inhibitor.

29 Claims, 7 Drawing Sheets
Specification includes a Sequence Listing.

(56) References Cited

OTHER PUBLICATIONS

Chang et al., "Characterization of the Binding of [3H]-(+/−)-L-364,718: a New Potent, Nonpeptide Cholecystokinin Antagonist Radioligand Selective for Peripheral Receptors", Molecular Pharmacology, vol. 30, 1986, pp. 212-217.
Corbett et al., "Induction and Chemotherapeutic Response of Two Transplantable Ductal Adenocarcinomas of the Pancreas in C57BL/6 Mice", Cancer Research, vol. 44, Feb. 1984, pp. 717-726.
Cox et al., "Molecular Pathways: Connecting Fibrosis and Solid Tumor Metastasis", Clinical Cancer Research, 2014, pp. 3637-3643.
Fang et al., "Targeting the Tumor Microenvironment: From Understanding Pathways to Effective Clinical Trials", Cancer Research, vol. 73, No. 16, Aug. 15, 2013, 18 pages.
Fino et al., "Downregulation of the CCK-B Receptor in Pancreatic Cancer Cells Blocks Proliferation and Promotes Apoptosis", Physiology Gastrointestinal Liver Physiology, vol. 302, No. 11, Jun. 1, 2012, pp. 1-11.
Hahne et al., "Proglumide and Benzotript: Members of a Different Class of Cholecystokinin Receptor Antagonists", Proceedings of the National Academy of Sciences of the United States of America, vol. 78, No. 10, Oct. 1981, pp. 6304-6308.
Hanyu et al., "Effect of Two New Cholecystokinin Antagonists on Gallbladder Emptying in Opossums", American Journal of Physiology, vol. 260, 1991, pp. G258-G264.
Herranz, "Cholecystokinin Antagonists: Pharmacological and Therapeutic Potential", Medicinal Research Reviews, vol. 23, Sep. 2003, pp. 559-605.
Hingorani et al., "Phase Ib Study of PEGylated Recombinant Human Hyaluronidase and Gemcitabine in Patients with Advanced Pancreatic Cancer", Clinical Cancer Research, vol. 22, No. 12, Jun. 15, 2016, pp. 2848-2855.
Howatson et al., "Pancreatic Carcinogenesis-Enhancement by Cholecystokinin in The Hamster-Nitrosamine Model", British Journal of Cancer, vol. 51, No. 1, Jan. 1985, pp. 107-114.
Kaczanowska et al., "TLR Agonists: Our Best Frenemy in Cancer Immunotherapy", Journal of Leukocyte Biology, vol. 93, No. 6, Jun. 2013, pp. 847-863.
Kennedy et al., "Central Role for the Cardiotonic Steroid Marinobufagenin in the Pathogenesis of Experimental Uremic Cardiomyopathy", Hypertension, vol. 47, No. 3, Apr. 2006, pp. 488-495.
Longnecker et al., "Carcinogenicity in Rats of the Nitrosourea Amino Acid N delta-(N-methyl-N-nitrosocarbamoyl)-L-ornithine", Journal of Environmental Pathology, Toxicology, vol. 4, No. 1, Aug. 1980, pp. 117-129.
Matters et al., "Cholecystokinin Mediates Progression and Metastasis of Pancreatic Cancer Associated with Dietary Fat", Digestive Diseases and Sciences, vol. 59, No. 6, Jun. 2014, pp. 1180-1191.
Matters et al., "Growth of Human Pancreatic Cancer is Inhibited by Down-regulation of Gastrin Gene Expression", Pancreas, vol. 38, 2009, pp. e151-e161.
Miederer et al., "Efficient Treatment of Gastric Ulcer with Proglumide (Milid) in Outpatients (Double Blind Trial)", Acta Hepatogastroenterol (Stuttg), vol. 26, 1979, pp. 314-318.
Mkrtichyan et al., "Anti-PD-1 Synergizes with Cyclophosphamide to Induce Potent Anti-tumor Vaccine Effects Through Novel Mechanisms", European Journal of Immunology, vol. 41, No. 10, Oct. 2011, pp. 2977-2986.
Nywening et al., "Phase 1b Study Targeting Tumour Associated Macrophages with CCR2 Inhibition Plus Folfirinox in Locally Advanced and Borderline Resectable Pancreatic Cancer", Lancet Oncology, vol. 17, No. 5, May 2016, pp. 651-662.
Nywening et al., "Targeting Tumour-Associated Macrophages with CCR2 Inhibition in Combination With Folfirinox in Patients With Borderline Resectable and Locally Advanced Pancreatic Cancer: A Single-centre, Open-label, Dose-finding, Non-randomised, Phase 1b Trial", The Lancet Oncology, vol. 17, No. 5, May 2016, pp. 651-662.
Application No. PCT/US2018/022617, International Preliminary Report on Patentability, dated Sep. 26, 2019, 6 pages.

Application No. PCT/US2018/022617, International Search Report and Written Opinion, dated Jun. 1, 2018, 9 pages.
Phillips et al., "Pancreatic Stellate Cells Produce Acetylcholine and May Play a Role in Pancreatic Exocrine Secretion", Proceedings of the National Academy of Sciences of the United States of America vol. 107, No. 40, Oct. 5, 2010, pp. 17397-17402.
Prasad et al., "Gene Expression Profiles in Pancreatic Intraepithelial Neoplasia Reflect the Effects of Hedgehog Signaling on Pancreatic Ductal Epithelial Cells", Cancer Research, vol. 65, No. 5, Mar. 1, 2005, pp. 1619-1626.
Rai et al., "Heterogeneous Expression of Cholecystokinin and Gastrin Receptor in Stomach and Pancreatic Cancer: An Immunohistochemical Study", Journal of Cancer Research and Therapeutics, vol. 12, 2016, pp. 411-416.
Sideras et al., "Role of the Immune System in Pancreatic Cancer Progression and Immune Modulating Treatment Strategies", Cancer Treatment Reviews, vol. 40, No. 4, May 2014, pp. 513-522.
Singh et al., "Novel Gastrin Receptors Mediate Mitogenic Effects of Gastrin and Processing Intermediates of Gastrin on Swiss 3T3 Fibroblasts", The Journal of Biological Chemistry, vol. 270, No. 15, Apr. 14, 1995, pp. 8429-8438.
Smith et al., "A Single Nucleotide Polymorphism of The Cholecystokinin-B Receptor Predicts Risk for Pancreatic Cancer", Cancer Biology and Therapy, vol. 13, No. 3, Feb. 1, 2012, pp. 164-174.
Smith et al., "CCK Stimulates Growth of Six Human Pancreatic Cancer Cell Lines in Serum-free Medium", Regulatory Peptides, vol. 32, No. 3, Feb. 26, 1991, pp. 341-349.
Smith et al., "Characterization of the CCK-C (Cancer) Receptor in Human Pancreatic Cancer", International Journal of Molecular Medicine, vol. 10, 2002, pp. 689-694.
Smith et al., "Cholecystokinin and Pancreatic Cancer: The Chicken or The Egg?", American Journal of Physiology Gastrointestinal and Liver Physiology, vol. 306, No. 2, Jan. 15, 2014, 14 pages.
Smith et al., "Cholecystokinin Receptor Antagonist Halts Progression of Pancreatic Cancer Precursor Lesions and Fibrosis in Mice", Pancreas, vol. 43, No. 7, Oct. 2014, pp. 1050-1059.
Smith et al., "Cholecystokinin Receptors and Panc-1 Human Pancreatic Cancer Cells", American Journal of Physiology, vol. 265, Jul. 1993, pp. G149-G155.
Smith et al., "Cholecystokinin Stimulates Growth of Human Pancreatic Adenocarcinoma SW-1990", Digestive Diseases and Sciences, vol. 35, No. 11, Nov. 1990, pp. 1377-1384.
Smith et al., "Combination Therapy with Immune Checkpoint Inhibitor and CCK-Receptor Blockade Increases Survival of Pancreatic Cancer", American Association for Cancer Research, Jul. 2016, 1 page.
Smith et al., "Gastrin Regulates Growth of Human Pancreatic Cancer in a Tonic and Autocrine Fashion", American Journal of Physiology, vol. 270, May 1996, pp. R1078-R1084.
Smith et al., "Identification and Characterization of CCK-B/gastrin Receptors in Human Pancreatic Cancer Cell lines", American Journal of Physiology, vol. 266, Jan. 1994, pp. R277-R283.
Smith et al., "Identification of Gastrin as a Growth Peptide in Human Pancreatic Cancer", American Journal of Physiology, vol. 268, 1995, pp. R135-R141.
Smith et al., "Quantitative Analysis of Gastrin mRNA and Peptide in Normal and Cancerous Human Pancreas", International Journal of Molecular Medicine, vol. 2, No. 3, Sep. 1998, pp. 309-315.
Strauss et al., "Targeting the Microenvironment of Pancreatic Cancer: Overcoming Treatment Barriers and Improving Local Immune Responses", Clinical Translational Oncology, vol. 18, No. 7, Jul. 2016, pp. 653-659.
Surana et al., "IL4 Limits the Efficacy of Tumor-Targeted Antibody Therapy in a Murine Model", Cancer Immunology Research, vol. 2, No. 11, Nov. 2014, pp. 1103-1112.
Tamiolakis et al., "Does Neoplastic Gastrin Expression Remodel the Embryonal Pattern of The Protein? A Study in Human Pancreas", Hepatogastroenterology, vol. 51, No. 55, 2004, pp. 249-252.
Wank et al., "Cholecystokinin Receptor Family. Molecular Cloning, Structure, and Functional Expression in Rat, Guinea Pig, and Human", Annals of the New York Academy of Sciences, vol. 713, Mar. 1994, pp. 49-66.

(56) References Cited

OTHER PUBLICATIONS

Wank et al., "Purification, Molecular Cloning, and Functional Expression of the Cholecystokinin Receptor from Rat Pancreas", Proceedings of the National Academy of Sciences of the United States of America vol. 89, Apr. 1992, pp. 3125-3129.

Weinberg et al., "Cholecystokinin A and B Receptors are Differentially Expressed In Normal Pancreas and Pancreatic Adenocarcinoma", Journal of Clinical Investigation, vol. 100, No. 3, Aug. 1997, pp. 597-603.

Zhang et al., "Cholecystokinin Octapeptide Regulates Lipopolysaccharide-activated B Cells Co-stimulatory Molecule Expression and Cytokines Production in Vitro", Immunopharmacology and Immunotoxicology, vol. 33, Mar. 2011, pp. 157-163.

Zhang et al., "Cholecystokinin Octapeptide Regulates the Differentiation and Effector Cytokine Production of CD4 T Cells In Vitro", International Immunopharmacology, vol. 20, No. 2, Jun. 2014, pp. 307-315.

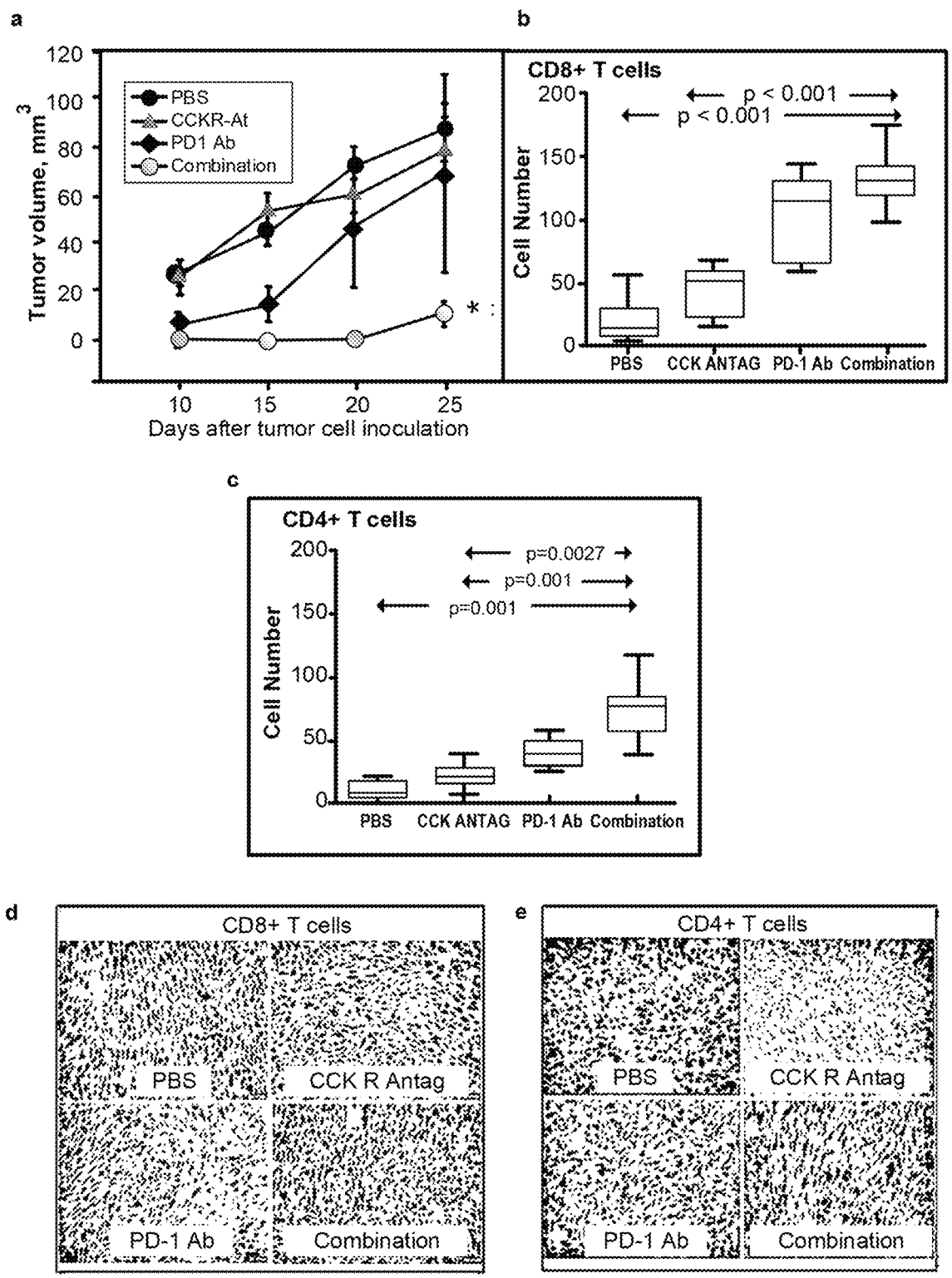
FIGS. 2a-e

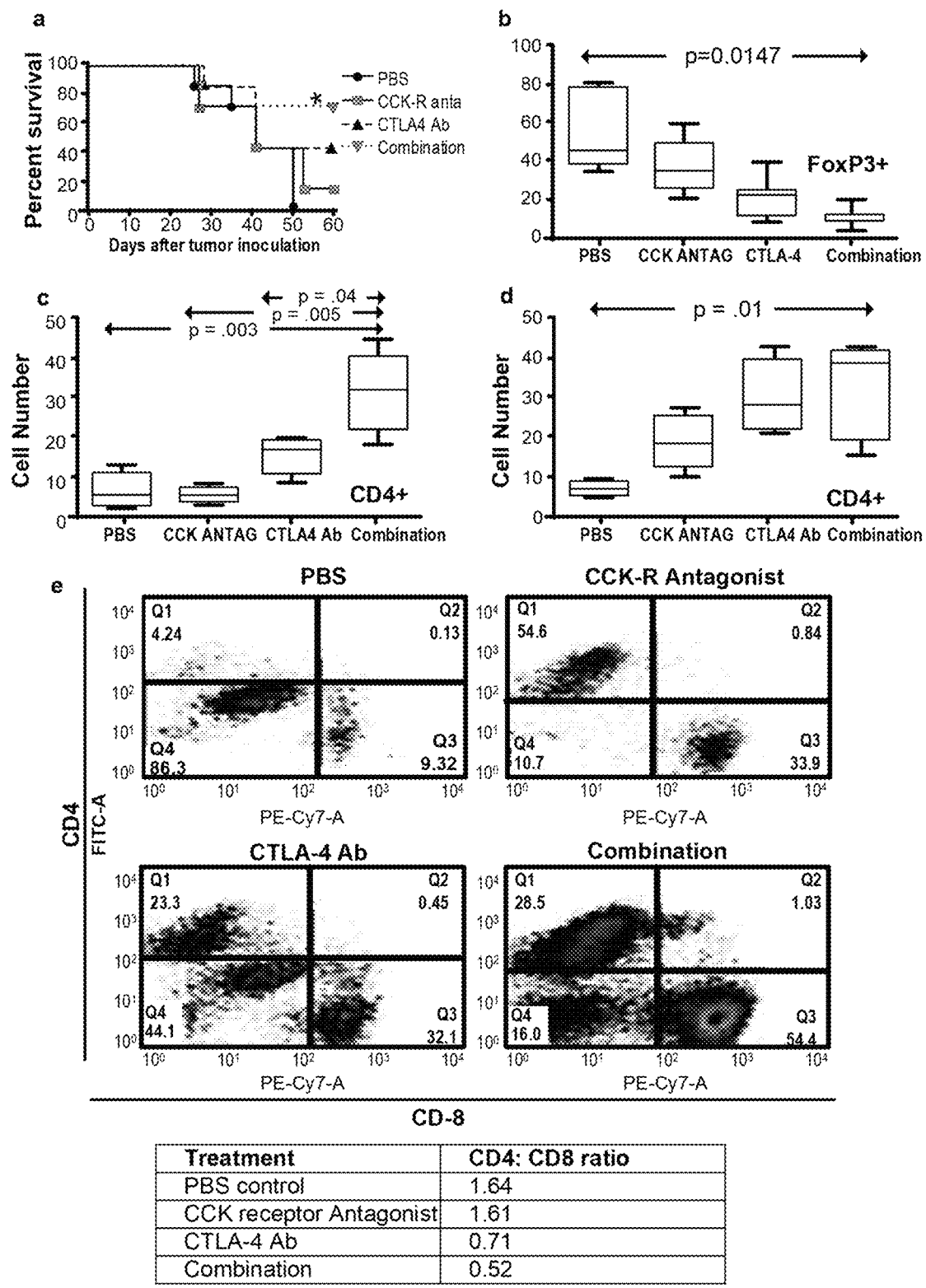
FIGS. 3a-e

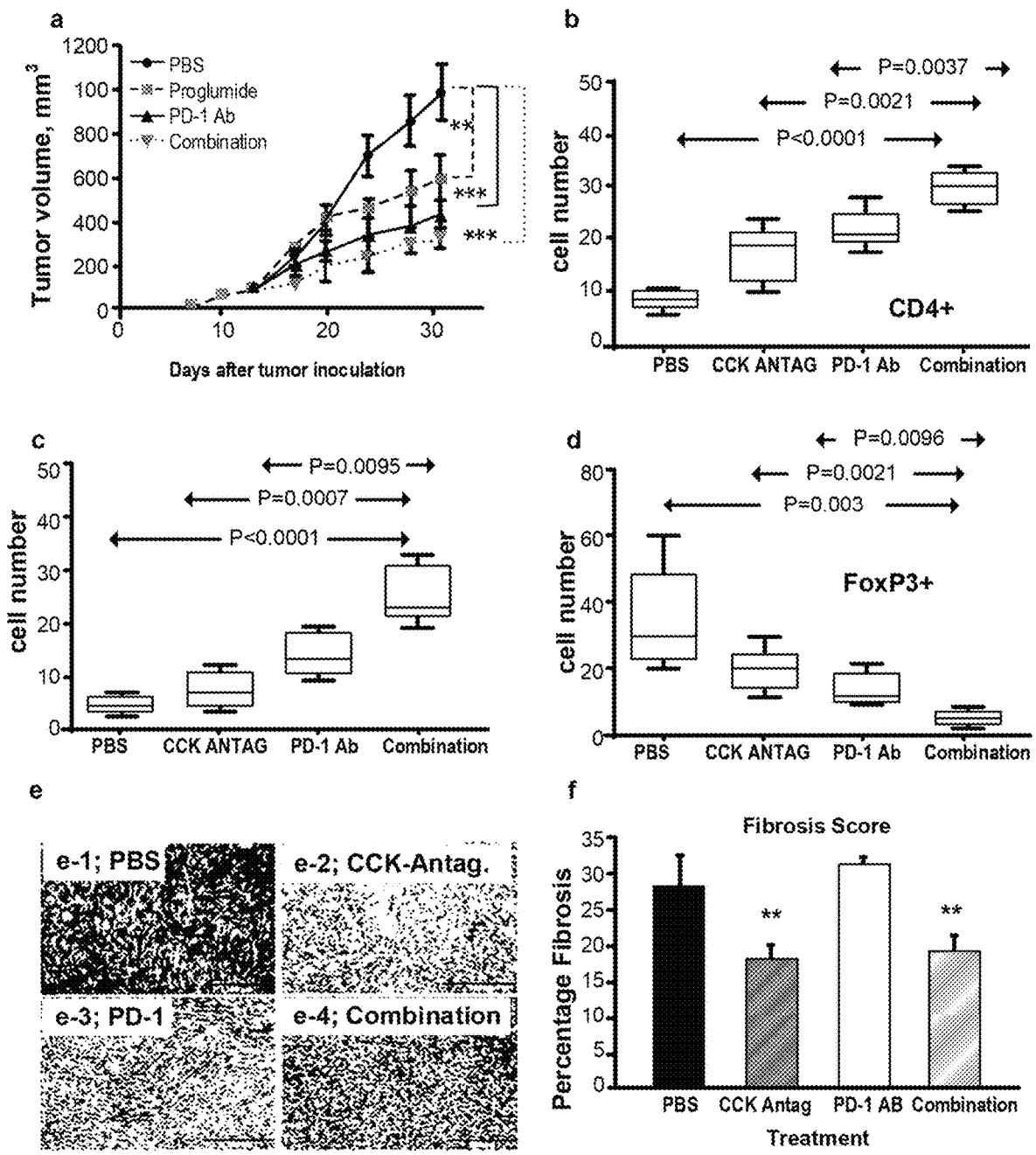
FIGS. 4a-f

TREATING CANCER WITH A CCK RECEPTOR INHIBITOR AND AN IMMUNE CHECKPOINT INHIBITOR

CROSS-REFERENCE TO PRIORITY APPLICATIONS

This application claims priority to U.S. Provisional Application No. 62/471,761, filed Mar. 15, 2017, the entirety of which is incorporated by reference herein.

STATEMENT REGARDING FEDERALLY FUNDED RESEARCH

This invention was made with government support under grant numbers CA050633 and CA194745 awarded by the National Institutes of Health. The government has certain rights in the invention.

BACKGROUND

Despite advances in diagnosis and treatment of other cancers over the years, no improvement has occurred in the survival of pancreatic cancer which carries the poorest prognosis of all gastrointestinal malignancies. A recent review of trends for cancer incidence and survival estimates that by the year 2020, pancreatic ductal adenocarcinoma (PDAC) will surpass colon and breast cancer to become one of the top two causes of cancer-related deaths in the USA. In fact currently, the 5-year survival rate for pancreatic cancer is about 5-6%, the lowest of any cancer. The reasons for the poor survival rates reported for pancreatic cancer include both the inability to diagnose this disease and intervene in the early stages and the relative resistance of PDAC to standard chemotherapy and immunotherapy.

SUMMARY

Provided herein are methods for treating a cholecystokinin (CCK) receptor-expressing cancerous tumor in a subject. The methods comprise administering a CCK receptor inhibitor and an immune checkpoint inhibitor to the subject.

Also provided are methods for increasing sensitivity of a (CCK) receptor-expressing cancerous tumor in a subject to immunotherapy. The methods comprise administering to the subject a CCK receptor inhibitor prior to administering an immunotherapy to the subject.

BRIEF DESCRIPTION OF THE FIGURES

FIGS. 2a-e show that combination therapy with PD-1 antibody and CCKR antagonist inhibits pancreatic cancer growth. (a) Tumor volumes were not significantly smaller in immune competent mice treated with PD-1 antibody or CCKR antagonist monotherapy (L-364,718) compared to PBS treated controls. In contrast, tumor volumes of mice receiving both the CCKR antagonist and the immune checkpoint blockade antibody were significantly smaller (*$p<0.05$). (b) The number of CD8+ cells significantly increased in mice treated with the combination therapy. (c) CD4+ cells in the tumors also increased in number with combination therapy. (d) Immunohistochemistry of mouse Panc02 tumors shows positive immunoreactivity for CD8+ cells with each treatment and the greatest in the combination group. (e) Immunohistochemistry of tumors demonstrates CD4+ stained cells for each treatment (mag 20x).

FIGS. 3a-e show the effects of CCKR blockade with L364,718 and CTLA-4 antibody on survival and tumor immune cells. (a) Kaplan Meier survival curve for immune competent C57BL/6 mice bearing Panc02 subcutaneous tumors show that all control animals (PBS) had died by day 50 when 42% of the CCKR-antagonist (CCK) treated, 42% of the CTLA4-Ab (CTLA4) treated, and 71% of the combination treated mice were still alive (*$p<0.05$). (b) Foxp3+ (Tregs) immune cells decrease in the tumor microenvironment with combination therapy. (c) CD8+ cell numbers increased in pancreatic cancer treated with the combination of CTLA-4 immune checkpoint blockade antibody and CCKR antagonism. (d) CD4+ cell numbers were increased also in tumors of mice treated with the combination of the CCKR antagonist and a CTLA-4 immune checkpoint blockade antibody. (e) CD4+ and CD8+ tumor infiltrating lymphocytes analysis by flow cytometry. Although both populations of T cells increased with therapy, the increase in the number of infiltrating CD8+ cells was greater. The CD4:CD8 ratio decreased significantly with the combination therapy using both the CCK receptor antagonist and the CTLA-4 antibody.

FIGS. 4a-f show the effects of CCKR blockade with proglumide and PD-1 antibody on growth of mT3 murine pancreatic cancer. (a) Growth curves over time shows that CCKR antagonist monotherapy ($p<0.01$), PD-1 monotherapy (*$p<0.001$), combination therapy (*$p<0.001$) significantly slowed tumor growth of mT3 tumors compared to PBS controls. (b) CD4+ tumor infiltrating lymphocytes increased with each of the treatment compared to PBS control treated mice. (c) CD8+ tumor infiltrating lymphocytes increase with each of the treatment compared to PBS. (d) Foxp3+ (Tregs) decrease with each of the treatments compared to PBS control treated mice. (e) Control treated mice mT3 tumors also exhibited dense fibrosis as shown by Masson's trichrome stain (e-1). Fibrosis was decreased in tumors of mice treated with the CCKR antagonist (e-2) but not in tumors of mice treated with PD-1 antibody monotherapy (e-3). Combination treatment decreased tumor-associated fibrosis similar to that of proglumide-treated mice (e-4). (f) Quantitative analysis of intratumoral fibrosis demonstrated significant differences in mice treated with proglumide by Kruskal-Wallis analysis (p<0.01).

DETAILED DESCRIPTION

Figures 1A, 1B, 1C, 1D, 1E, 1F, 1G:
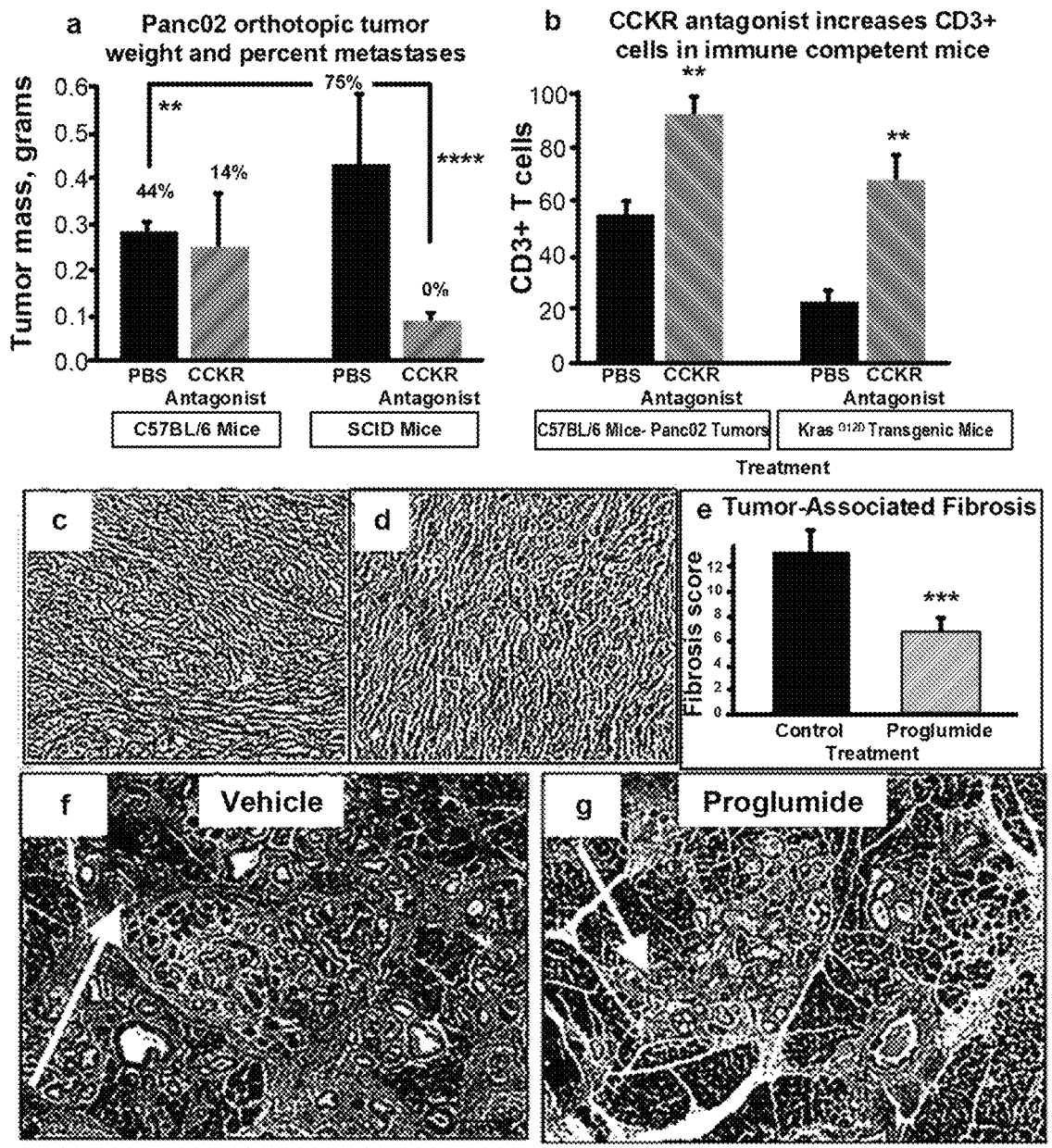
FIGS. 1a-g show that monotherapy with CCKR antagonist inhibits primary tumor growth and alters the pancreas microenvironment. (a) Panc02 pancreatic cancer growth is increased in SCID mice compared to C57BL/6 mice ($p<0.01$). Tumor growth is suppressed in SCID mice when the animals are treated with a CCK receptor antagonist ($p<0.0001$) but not in the immune competent mice. The percentage of mice with metastases is shown above each respective column. CCKR antagonist therapy reduced metastases in C56BL/6 mice and there were no metastases in SCID mice treated with the CCKR antagonist. (b) CD3+ tumor infiltrating lymphocytes significantly increase in the pancreatic cancer microenvironment with CCKR antagonist treatment in both C57BL/6 mice bearing Panc02 tumors and in the mutant KRAS transgenic mice ($p<0.01$). (c) Trichrome stain of Panc02 tumor from a vehicle-treated mouse demonstrating marked fibrosis. (d) Trichrome stain of a Panc02 tumor from a mouse treated with the CCKR antagonist proglumide demonstrates marked decreased fibrosis. (e) Quantitation of fibrosis from Panc02 tumors of untreated mice (control) is significantly greater than tumors of mice treated with proglumide (***$p<0.001$). (f) Trichrome stain of a pancreas from the control mutant KRAS transgenic mouse shows extensive fibrosis. (g) Trichrome stain from an age-matched mutant KRAS transgenic mouse that was treated with the CCK receptor antagonist proglumide, showed significantly diminished fibrosis.

Provided herein is a method for treating a cholecystokinin (CCK) receptor-expressing cancerous tumor in a subject, comprising administering to the subject an effective amount of a CCK receptor inhibitor and an effective amount of an immune checkpoint inhibitor.

Also provided is a method for increasing sensitivity of a (CCK) receptor-expressing cancerous tumor in a subject to immunotherapy, the method comprising administering to the subject an effective amount of a CCK receptor inhibitor prior to administering to the subject an immunotherapy.

In any of the methods provided herein, the CCK receptor-expressing cancerous tumor can be, but is not limited to, a gastrointestinal tumor. In the methods provided herein, the cancerous tumor can express one or more CCK receptors selected from the group consisting of a CCK-A receptor (CCK1R), a CCK-B receptor (CCK2R) and a CCK-C receptor.

For example, and not to be limiting, in the methods provided herein, the CCK receptor-expressing cancerous tumor can be a tumor in the pancreas, esophagus, gallbladder liver, stomach, small intestine, bowel (large intestine, colon or rectum) or anus of the subject. In any of the methods provided herein, the pancreatic tumor can be a pancreatic ductal adenocarcinoma (PDAC).

In any of the methods provided herein, the CCK receptor inhibitor or antagonist can be a CCK receptor inhibitor or antagonist that inhibits one or more CCK receptors selected from the group consisting of a CCK-A receptor, a CCK-B receptor and a CCK-C receptor. In any of the methods provided herein, the CCK receptor antagonist can decrease the fibrosis of the tumor, thus altering the microenvironment of the tumor. As used throughout, fibrosis, for example, refers to a process resulting in excess deposition of extracellular matrix components, for example, collagen. See, for example, Cox and Erler "Molecular Pathways: Connecting Fibrosis and Solid Tumor Metastasis," *Clin Cancer Res;* 20 (14); 3637-43, hereby incorporated in its entirety by this reference. In any of the methods provided herein, a decrease in fibrosis can be a decrease of about 10, 20, 30, 40, 50, 60, 70, 80, 90% or greater when compared to the subject prior to treatment or when compared to a control subject or control value. Optionally, administration of the CCK receptor antagonist and an immune checkpoint inhibitor to the subject increases the number of CD8+ cells and/or CD4+ cells in the cancerous tumor.

Also provided is a method of treating fibrosis in a subject. The method comprises administering an effective amount of a CCK receptor inhibitor to the subject. In the method of treating fibrosis, fibrosis can be decreased by about 10, 20, 30, 40, 50, 60, 70, 80, 90% or greater when compared to the subject prior to treatment or when compared to a control subject or control value. In some examples, the fibrosis is in an organ or tissue that is not associated with a CCK receptor expressing cancerous tumor in the subject. In some examples, the fibrosis is pancreatic fibrosis. In other examples, the fibrosis is a non-pancreatic fibrosis, for example, fibrosis of the lung, liver or kidney. In some examples, the CCK receptor inhibitor inhibits the CCK receptor on fibroblasts in the fibrotic tissue or organ.

In some examples, the CCK receptor inhibitor or antagonist inhibits the CCK-A receptor and the CCK-B receptor. For example, and not to be limiting, proglumide can be used to inhibit both the CCK-A receptor and the CCK-B receptor. Therefore, in any of the methods provided herein, an immune checkpoint inhibitor can be administered to the subject with a CCK-A receptor antagonist, a CCK-B receptor antagonist, a CCK-C receptor antagonist, an antagonist that inhibits both the CCK-A receptor and the CCK-B receptor, an antagonist that inhibits both the CCK-A receptor and the CCK-C receptor, an antagonist that inhibits both the CCK-B receptor and the CCK-C receptor or an antagonist that inhibits the CCK-A receptor, the CCK-B receptor and the CCK-C receptor.

In some examples, the CCK receptor inhibitor or antagonist selectively or preferentially inhibits the CCK-A receptor, the CCK-B receptor or the CCK-C receptor. An example of a CCK receptor antagonist that selectively or preferentially inhibits the CCK-A receptor, is L364,718 (Devazepide). Other examples of antagonists that preferentially inhibit the CCK-A receptor include, but are not limited to Lorglumide, Loxiglumide, Dexloxiglumide, and Lintript (See Berna et al. *Curr. Top. Med. Chem.* 7 (12): 1211-1231 (2007)), hereby incorporated in its entirety by this reference). Examples of antagonists that preferentially inhibit the CCK-B receptor include, but are not limited to, Spiroglumide, Itriglumide, CI-988, L365,260 and YF476 (See Berna et al.)

Examples of immune checkpoint inhibitors that can be used in any of the methods provided herein include, but are not limited to, a programmed cell death protein 1 (PD-1) inhibitor, a cytotoxic T-lymphocyte-associated antigen 4 (CTLA-4) inhibitor, a programmed death-ligand 1 inhibitor (PD-L1), a lymphocyte activation gene 3 (LAG-3) inhibitor, a B- and T-lymphocyte attenuator (BTLA) inhibitor, an adenosine A2A (A2aR) inhibitor, or a B-7 family inhibitor. In some methods, the PD-1 inhibitor is an anti-PD-1 antibody. For example, and not to be limiting, the anti-PD-1 inhibitor can be selected from the group consisting of nivolumab, pembrolizumab, durvalumab, and pidilizumab. In some methods, the anti-CTLA-4 inhibitor is an anti-CTLA-4 antibody. For example, and not to be limiting, the CTLA-4 inhibitor can be ipilimumab or tremelimumab.

In any of the methods provided herein, the CCK receptor-expressing cancerous tumor can be a CCK receptor-expressing cancerous tumor that is resistant to immunotherapy. For example, the a CCK receptor-expressing cancerous tumor can be a tumor in the pancreas, esophagus, gallbladder liver, stomach, small intestine, bowel (large intestine, colon or rectum) or anus of the subject that is resistant to immunotherapy.

As used throughout, immunotherapy is a therapy that uses the subject's own immune system to treat cancer in the subject. Examples of cancer immunotherapy include, but are not limited to, monoclonal antibodies, immune checkpoint inhibitors, cancer vaccines, cytokines and interferons.

In some methods, the subject is resistant to treatment with one or more immune checkpoint inhibitors. For example, the subject can be resistant to treatment with one or more of a programmed cell death protein 1 (PD-1) inhibitor, a cytotoxic T-lymphocyte-associated antigen 4 (CTLA-4) inhibitor, a programmed death-ligand 1 inhibitor (PD-L1), a lymphocyte activation gene 3 (LAG-3) inhibitor, a B- and T-lymphocyte attenuator (BTLA) inhibitor, an adenosine A2A (A2aR) inhibitor, or a B-7 family inhibitor. In some methods, the PD-1 inhibitor is an anti-PD-1 antibody. For example, and not to be limiting, the anti-PD-1 inhibitor can be selected from the group consisting of nivolumab, pembrolizumab and pidilizumab. In other methods, the anti-CTLA-4 inhibitor is an anti-CTLA-4 antibody. For example, and not to be limiting, the CTLA-4 inhibitor can be ipilimumab or tremelimumab.

Any of the methods provided herein can further comprise administering one or more chemotherapeutic agents to the subject. The chemotherapeutic can be administered prior to, concurrently with or subsequent to treatment with a CCK receptor inhibitor and/or a checkpoint inhibitor. The chemotherapeutic agents that can be used include, but are not limited to, antineoplastic agents such as Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; 5-Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin C; Mitosper; Mitotane; Mitoxantrone; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

In any of the methods provided herein, where a chemotherapeutic agent is administered, the chemotherapeutic agent can be selected from the group consisting of paclitaxel, gemcitabine, fluorouracil and irinotecan. Any of the methods provided herein can optionally further include administering radiation therapy to the subject.

The methods provided herein can further comprise diagnosing the subject with a CCK receptor-expressing cancerous tumor and/or determining the sensitivity of the subject to immunotherapy.

Throughout, treat, treating, and treatment refer to a method of reducing or delaying one or more effects or symptoms of a CCK receptor-expressing cancer. The subject can be diagnosed with a CCK receptor-expressing cancer prior to treatment. Treatment can also refer to a method of reducing the underlying pathology rather than just the symptoms. The effect of the administration to the subject can have the effect of, but is not limited to, reducing one or more symptoms (e.g., reduced pain, reduced size of the tumor, etc.) of the cancer, a decrease in fibrosis in the tumor, an increase in survival time, a reduction in the severity of the cancer (e.g., reduced rate of growth of a tumor or rate of metastasis), the complete ablation of the cancer, or a delay in the onset or worsening of one or more symptoms. For example, a disclosed method is considered to be a treatment if there is about a 10% reduction in one or more symptoms of the disease in a subject when compared to the subject prior to treatment or when compared to a control subject or control value. Thus, the reduction can be about a 10, 20, 30, 40, 50, 60, 70, 80, 90, 100%, or any amount of reduction in between.

As used throughout, an increase in sensitivity of a (CCK) receptor-expressing cancerous tumor in a subject to immunotherapy, refers to an increase in the subject's response to immunotherapy. The increase can be an increase of about 10, 20, 30, 40, 50, 60, 70, 80, 90, 100, 200, 300, 400, 500%, or greater, as compared to the sensitivity of the subject to the immunotherapy in the absence of treatment with one or more CCK-R antagonists.

As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

The term effective amount, as used throughout, is defined as any amount necessary to produce a desired physiologic response.

Exemplary dosage amounts for administration of a CCK receptor antagonist or an immune checkpoint inhibitor in a mammal include doses from about 0.5 to about 200 mg/kg of body weight of active compound per day, which may be administered in a single dose or in the form of individual divided doses, such as from 1 to 4 times per day can be used. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 50 mg/kg of body weight of active compound per day, about 1 to about 40 mg/kg of body weight of active compound per day, about 1 to about 30 mg/kg of body weight of active compound per day, about 1 to about 30 mg/kg of body weight of active compound per day, about 30 mg/kg of body weight of active compound per day about 20 mg/kg of body weight of active compound per day, about 10 mg/kg of body weight of active compound per day, or about 5 mg/kg of body weight of active compound per day. One of skill in the art would adjust the dosage as described below based on specific characteristics of the inhibitor and the subject receiving it.

Effective amounts and schedules for administering a CCK receptor antagonist and an immune checkpoint inhibitor can be determined empirically and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, unwanted cell death, and the like. Generally, the dosage will vary with the type of inhibitor, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily.

The CCK-R antagonists and immune checkpoint inhibitors described herein can be provided in a pharmaceutical composition. These include, for example, a pharmaceutical composition comprising a therapeutically effective amount of one or more CCK-R antagonists and a pharmaceutical carrier; a pharmaceutical composition comprising a therapeutically effective amount of one or more immune checkpoint inhibitors and a pharmaceutical carrier; and a pharmaceutical composition comprising a therapeutically effective amount of one or more CCK-R antagonists, one or more immune checkpoint inhibitors and a pharmaceutical carrier.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012).

Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

The compositions are administered in a number of ways depending on whether local or systemic treatment is desired, and on the area to be treated. The compositions are administered via any of several routes of administration, including orally, parenterally, intravenously, intraperitoneally, intramuscularly, subcutaneously, intrarectally, intracavity or transdermally. Pharmaceutical compositions can also be delivered locally to the area in need of treatment, for example by topical application or local injection. Effective doses for any of the administration methods described herein can be extrapolated from dose-response curves derived from in vitro or animal model test systems.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Advanced pancreatic ductal adenocarcinoma (PDAC) has typically been resistant to chemotherapy and immunotherapy; therefore, novel strategies are needed to enhance therapeutic response. Cholecystokinin (CCK) is a gastrointestinal peptide involved in digestion, but has also been shown to promote pancreatitis and stimulate growth of pancreatic cancer. CCK receptors (CCKRs) are present on pancreatic cancer epithelial cells, fibroblasts of the microenvironment, and lymphocytes. In this investigation, the role of CCK receptor blockade monotherapy or immune checkpoint blockade antibodies alone or in combination was examined in murine models of a PDAC.

Methods

Cell Lines—Panc02 cells, a murine pancreatic cancer cell line which is syngeneic to C57BL/6 mice, (Corbett et al. Induction and chemotherapeutic response of two transplantable ductal adenocarcinomas of the pancreas in C57BL/6 mice. *Cancer Res* 44:717-26 (1984)) were a gift from Professor Corbett (Wayne State University, Mich., USA). The Panc02 cells were developed by implanting a carcinogen (3-methyl-cholanthrene) coated thread into the mouse pancreas. Cells were cultured in DMEM: F12 media with 10% FBS. Histologically, Panc02 cancer cells resemble human pancreatic cancer in that they are ductal epithelium; in vivo, the tumors are locally invasive and metastatic, and Panc02 tumors are associated with a dense fibrotic microenvironment. CCK receptors on Panc02 cells have been characterized by qRT-PCR and immunohistochemistry and are consistent with CCK-A receptors. In the following series of experiments Panc02 cells ($1 \times 10^6$ or $2 \times 10^6$) were injected either orthotopically or subcutaneously in animals.

The second cell line used in this investigation mT3-2D (mT3) was obtained from the laboratory of Dr. David Tuveson (Cold Spring Harbor, N.Y.) (Boj et al. "Organoid models of human and mouse ductal pancreatic cancer," *Cell* 160:324-338 (2015)). This murine pancreatic cancer cell line was developed from organoids isolated from mutant Kras$^{LSL-G12D}$; Pdx1-Cre mouse PDAC lesions and it has mutant KRAS, similar to human PDAC. The cell line is also syngeneic to C57BL/6 mice; and therefore, capable of being studied in immune competent mice.

Characterization of CCK receptors on mT3 pancreatic cancer cells—To confirm that mT3 cancer cells express CCKRs, total RNA was extracted from mT3 cells with an RNeasy Plus Mini Kit (Qiagen, Germantown, Md.) and 1 µg was subjected to RT-PCR in a SimpliAmp Thermal Cycler (Applied Biosystems, Carlsbad, Calif.) for evaluation of CCK-A and CCK-B receptor expression status. Reverse transcription was performed under the following conditions: 95° C.×30 sec (denaturation), 60° C.×1 min (annealing), and 72° C. for 30 sec (elongation)×35 cycles using murine CCK-A receptor primers: 5'CTTTTCTGCCTGGAT-CAACCT3' (forward) (SEQ ID NO: 1); 5'ACCGTGA-TAACCAGCGTGTTC3' (Reverse) (SEQ ID NO: 2). The murine primers for the CCK-B receptor were as follows: forward primer 5'GATGGCTGCTACGTGCAACT3'(SEQ ID NO: 3) and reverse primer 5'CGCACCACCCGCTTCT-TAG3' (SEQ ID NO: 4). HPRT was used as a reference gene and primers were: 5' TCCTCCTCAGACCGCTTT3' (forward) (SEQ ID NO: 5), 5' TTTTCCAAATCCTCGGCAT-AATG3' (reverse) (SEQ ID NO: 6). PCR products were evaluated by gel electrophoresis in a 2% agarose gel. Confirmation of CCK-B receptor protein expression was confirmed with immunofluorescence with CCK-B receptor antibody (1:200; Abcam ab77077, Toronto, Canada) conjugated to Dylight 488 (ab201799). Nuclei were stained with Hoescht: NucBlue™ (Thermofisher, Waltham, Mass.).

Animal Models—Three different murine models were used in this investigation: 1) severe combined immune deficiency (B6.CB17-Prkdc$^{scid}$/SzJ; SCID) mice to study the role of CCKR blockade on orthotopic cancer growth and metastasis independent of immune cells, 2) immune competent Pdx1-Cre/LSL-Kras$^{G12D}$ transgenic mice for a pancreatic carcinogenesis model to study the role of CCKR blockade on the pancreatic stellate cells and immune cells of the pancreas, and 3) immune competent C57BL/6 mice to study the role of CCKR antagonist in combination with immune checkpoint antibodies on growth and survival of mice bearing syngeneic PDAC tumors. Institutional guidelines for care and use of laboratory animals were followed throughout the study in accordance with protocols approved by the Georgetown University Institutional Animal Use and Care Committee.

This investigation was divided into several groups of experiments with different murine models of pancreatic cancer. In the following series of experiments Panc02 cells ($1\times10^6$) were injected either orthotopically as previously described (Matters et al. Growth of human pancreatic cancer is inhibited by down-regulation of gastrin gene expression," *Pancreas* 38: e151-e161 (2009)) or subcutaneously ($1\times10^6$ and $2\times10^6$) in mice. mT3 cells ($1\times10^5$) were grown subcutaneously in immune competent syngeneic mice. Subcutaneous tumor volumes were measured with calipers weekly in animals bearing subcutaneous tumors using the formula Length×(width)$^2$×0.5.

Treatments—Two different CCK receptor antagonists were used in this investigation. L-364,718 (Tocris Bioscience, Avonmouth, Bristol, United Kingdom) is a selective CCK-A receptor antagonist, which is the primary phenotype of the CCK receptors in Panc02 murine cancer cells. L364,718 was administered at a dose of 4 mg/kg three times a week by an intraperitoneal injection. The other CCK receptor antagonist used was proglumide which is an orally bioavailable nonselective antagonist that blocks both the CCK-A and CCK-B receptors. Proglumide (Tocris Bioscience) was administered in the drinking water at a concentration of 0.1 mg/mL, or approximately 30 mg/kg/d per mouse.

Two immune checkpoint blockade antibodies were used in this investigation. The antibody to the programmed cell death protein 1 (PD1-Ab) (Bio X cell, West Lebanon, N.H.) was administered intraperitoneally to mice at a dose of either 125 µg×3 injections or 200 µg every 3 days. The antibody to cytotoxic T-lymphocyte-associated antigen 4 (CTLA-4 Ab; Bio-X cell, West Lebanon, N.H.) was given at a dose of 200 µg every 3 days by intraperitoneal injections.

Study Design—To demonstrate the importance of the endogenous immune system in regulating growth and metastases of pancreatic cancer, tumor mass was compared four weeks after orthotopic inoculation of $10^6$ Panc02 cells in the pancreas of SCID (N=20) versus C57BL/6 mice (N=28). Ten mice in each group were treated with L364,718, (4 mg/kg) three times a week and the other mice were treated with PBS (controls). Four weeks after tumor inoculation mice were euthanized, tumors removed and weighed, and the number of metastases counted. TILs were evaluated in tumors of the C57BL/6 mice by immunohistochemistry and fibrosis assessed with Masson's trichrome stain.

The second series of experiments was performed to analyze the role of CCKR antagonist monotherapy on the TILs of the pancreas microenvironment during pancreatic carcinogenesis using the Pdx1-Cre/LSL-Kras$^{G12D}$ transgenic mouse. After the mice reached 3-4 months of age, when PanINs and fibrosis are established, mice were treated with either proglumide (in the drinking water) or untreated water. After 4 months of therapy, the pancreata were excised and compared to the pancreas of age-matched litter mates of mice on untreated water. Tissues were stained for fibrosis and CD3+ lymphocytes.

Another series of experiments was performed in C57BL/6 mice to evaluate the role of CCKR blockade in combination with immune checkpoint antibody therapy. Each series of experiments was performed using 40 mice with syngeneic murine tumors. The first two experiments tested the effects of L364,718 and the PD-1 Ab in mice injected with Panc02 cells ($1\times10^6$ or $2\times10^6$). The 3$^{rd}$ experimental design examined the role of the CTLA-4 Ab and proglumide in mice inoculated with $1\times10^6$ Panc02 cancer cells. In the 4$^{th}$ experiment, the mT3 cells ($1\times10^5$) were injected and mice were treated with PBS, proglumide, the PD-1 antibody, or the combination of both compounds. Animal treatments were initiated one week after cancer cell inoculation to assure all animals in the study had a measurable tumor and not to interfere with tumor initiation. The primary end point was tumor volume (1,000 mm$^3$) or mouse survival. Tumors were excised and examined histologically, and by immunohistochemistry, or by flow cytometry for immune cells.

Histology and Immunohistochemistry—Pancreatic tumors or whole pancreas (KRAS study) were excised after treatment and the tissues were paraffin embedded, sectioned, and stained with hematoxylin & eosin and Masson's trichrome stain for fibrosis evaluation. Some tumors were stained with an antibody to α-SMA (Abeam; Ab124964 at 1:6000). Tumor sections were also stained with either CD3 antibodies (1:85; DAKO, Carpinteria, Calif.); CD8 antibodies (1:75; eBioscience, San Diego, Calif.); CD4 antibodies (1:225; eBioscience), or FoxP3 antibody (1:30; eBioscience) and immunoreactive cells counted manually. Fibrosis was determined by Masson's trichrome staining, and a quantitative fibrosis analysis was done in a blinded fashion according to a previously described protocol (Kennedy et al. Central role for the cardiotonic steroid marinobufagenin in the pathogenesis of experimental uremic cardiomyopathy, *Hypertension* 47:488-95 (2006)).

Flow Cytometry—Tumors were harvested when they reached approximately 1000 mm$^3$ and were mechanically disrupted and subjected to enzymatic digest using a 1 mg/mL collagenase D solution (Roche). Red blood cells were lysed using a RBC lysis buffer (eBioscience). Cells were washed twice with RPMI+10% FBS and passed through a 70-µm cell strainer. The cell suspension was washed twice with ice-cold PBS and stained with LIVE/DEAD-Violet dye according to the manufacturer's recommendation (Life Technologies, Carlsbad, Calif.). Fc receptors were blocked using 1 µg anti-CD16/CD32 (BioLegend, San Diego, Calif.; TruStain FcX). Staining for surface antigens was performed in PBS+1% BSA using the following antibodies: CD3 (BioLegend; clone 145-2C11), CD4 (eBioscience; clone RM4-5), CD8 (BioLegend; clone 53-6).

Statistics—The results of immune cell analysis were expressed as means±standard error of the mean (SEM). Comparisons were made by ANOVA and student's t-test. Bonferroni corrections were made for multiple comparisons. Survival was analyzed by Kaplan Meier analysis and differences by hazard ratios using Prism Software (GraphPad software, Inc., San Diego, Calif.). Where data was skewed a nonparametric Kruskal-Wallis statistical method was performed.

Results

CCKR Antagonist Monotherapy Blocks Tumor Growth and Metastases.

Orthotopic Panc02 tumor weights were 2-3 fold greater in SCID mice compared to C57BL/6 mice (FIG. 1a) suggesting that the endogenous immune system in the wild type mouse is restraining tumor growth. The CCKR antagonist, L364,718, significantly reduced the primary tumor weight in SCID mice but not in immune competent mice. Seventy-five percent of the SCID mice had metastases to liver, mesenteric lymph nodes, and/or lung. There were no metastases in the SCID mice that were treated with the CCKR antagonist. Although CCKR antagonist therapy did not alter the primary tumor size in immune competent mice at the dose used, the CCKR antagonist decreased metastases. Since the CCKR antagonist monotherapy was effective in decreasing primary tumor growth in the immune deficient mouse, this suggests that inhibition of tumor growth and metastases with CCKR antagonism is at least in part independent of the host immune system.

CCKR Antagonist Monotherapy Significantly Modifies the Tumor Microenvironment.

Orthotopic tumors from the C57BL/6 immune competent mice were analyzed for tumor infiltrating lymphocytes. Mice treated with L364,718, had a significant increase in CD3+ lymphocytes by immunohistochemistry compared to the tumors from the PBS control mice (FIG. 1b). In the Pdx1-Cre/LSL-Kras$^{G12D}$ transgenic mouse experiments, the mice that received proglumide monotherapy exhibited a significant increase in the CD3+ cells in the mouse pancreas compared to control animals (FIG. 1b). Orthotopic Panc02 tumors from PBS treated mice showed extensive fibrosis in the tumor microenvironment (FIG. 1c) and this fibrosis was significantly decreased in tumors of the mice treated with CCKR blockade (FIG. 1d). Differences in mean fibrosis scores with CCKR treatment (FIG. 1e) were confirmed by quantitative analysis (Kennedy et al., "Central role for the cardiotonic steroid marinobufagenin in the pathogenesis of experimental uremic cardiomyopathy. *Hypertension* 47:488-495 (2006)). In the pancreatic carcinogenesis experiments using the mutant Pdx1-Cre/LSL-Kras$^{G12D}$ mouse, proglumide also significantly reversed fibrosis of the pancreas microenvironment (FIG. 1f, g). These data show that CCKR antagonist monotherapy alters the pancreas microenvironment by decreasing fibrosis Combination Therapy With CCK-Receptor Antagonist and PD-1 Immune Checkpoint Antibody Inhibits Growth of Pancreatic Cancer.

In the next series of experiments, whether CCKR antagonist therapy could improve responsiveness to immune checkpoint antibodies in immune competent mouse models was evaluated. Panc02 tumors increased in size in the mice treated with PBS (controls). The CCKR antagonist L364, 718 monotherapy, and PD-1 antibody monotherapy (at the lower dose—125 µg×3 injections), did not significantly decrease the tumor size (FIG. 2a). In contrast, mice receiving the combination of the CCKR antagonist and the PD-1 antibody had tumors 22-times smaller compared to the PBS group (FIG. 2a). Immunohistochemistry revealed a lack of CD8+ (FIG. 2b) and CD4+ (FIG. 2c) cells in the tumors from the PBS-control animals. Immunoreactivity for both CD4 and CD8 increased in tumors treated with the PD-1 antibody or the CCKR antagonist L364,718. The greatest number of CD8+ and CD4+ cells were noted in tumors of mice treated with the combination therapy. Individual group immunohistochemistry stains are shown for CD8+ tumor infiltrating lymphocytes (FIG. 2d) and CD4+ tumor infiltrating lymphocytes (FIG. 2e).

Effects of CCKR Blockade With Proglumide and PD-1 Antibody on Survival of Mice With Greater Tumor Burden.

Figure 5:
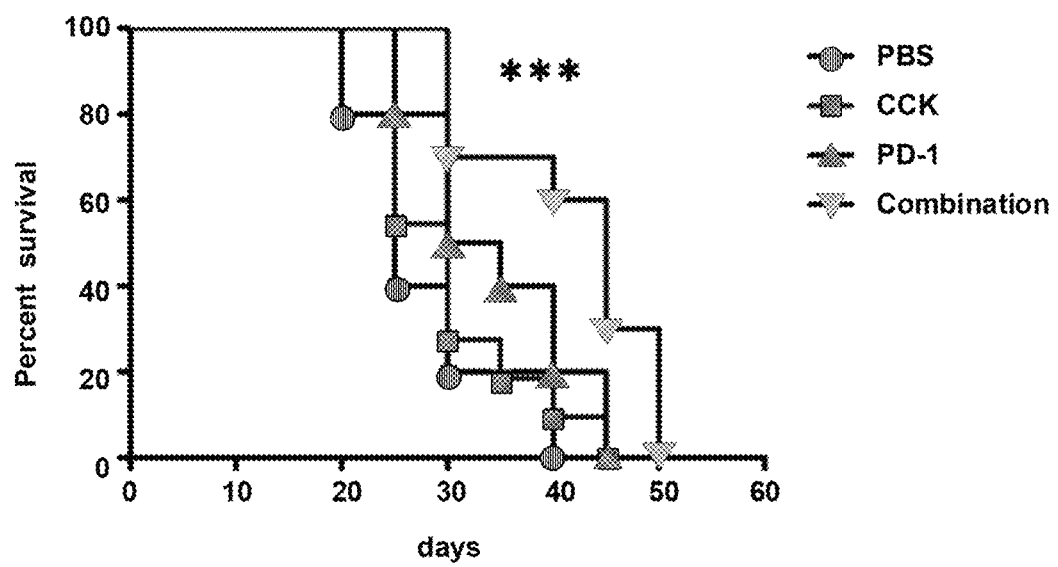
FIG. 5 shows a Kaplan Meier survival curve with Proglumide and PD-1 Ab. In this experiment, mice were inoculated with a greater number of Panc02 cancer cells ($2\times10^6$) and treated with either the PD-1 immune checkpoint antibody, proglumide, or the combination. Combination therapy with the CCK-receptor antagonist and the immune checkpoint blockade antibody rendered the longest survival (***p<0.001).

In another experiment immune competent mice received twice the number of Panc02 cells (2×10$^6$) to increase tumor burden. This experiment utilized the CCKR antagonist, proglumide and the PD-1 antibody. The Kaplan Meier survival curve for this experiment is shown in FIG. 5. On day 45 when all the PBS control treated mice had died, 60% of the mice treated with the combination of PD-1 antibody and proglumide were still alive (p=0.0009). Treatment with either PD-1 antibody or proglumide prolonged life by 5 days and the combination prolonged life by 10 days. This experiment demonstrates that even with a greater tumor burden, combination therapy with a CCKR antagonist and immune checkpoint antibody improves survival of mice bearing Panc02 pancreatic tumors.

Combination Therapy With CCKR-Antagonist L364,718 and CTLA-4 Immune Checkpoint Antibody Prolongs Survival of Panc02 Pancreatic Cancer-Bearing Mice.

Kaplan Meier analysis revealed improved survival of mice bearing Panc02 tumors treated with the combination of L36,718 and CTLA-4 Ab compared to PBS, or CCKR antagonist and CTLA-4 monotherapy (FIG. 3a). All PBS-treated control animals had died by day 50, while 42% of the CCKR antagonist treated, 42% of the CTLA4-Ab treated, and 71% of the combination treated mice were still alive (p<0.05). By day 90 only one mouse was still alive and it was in the combination-treated group.

Immunohistochemical stains of tumors obtained at necropsy showed that Foxp3+ cells were significantly increased in control mice (FIG. 3b). The number of Foxp3+ cells decreased with treatment and was significantly diminished in tumors of mice treated with the combination therapy (**p=0.0147). Average CD8+ (FIG. 3c) and average CD4+ (FIG. 3d) cell numbers were increased in the Panc02 tumors of mice treated with CCKR antagonism and CTLA-4 antibody, and markedly increased with the combination of both agents. Evaluation by flow cytometry confirmed the immunohistochemical stains (FIG. 3e). Since the number of CD8+ cells exceeded the influx of CD4+ cells, the CD4: CD8 ratio decreased with combination treatment.

CCKR Antagonist Proglumide and PD-1 Antibody Therapy Decrease Tumor Growth and Improve Survival in Mice With mT3 Pancreatic Cancers.

Figure 6:
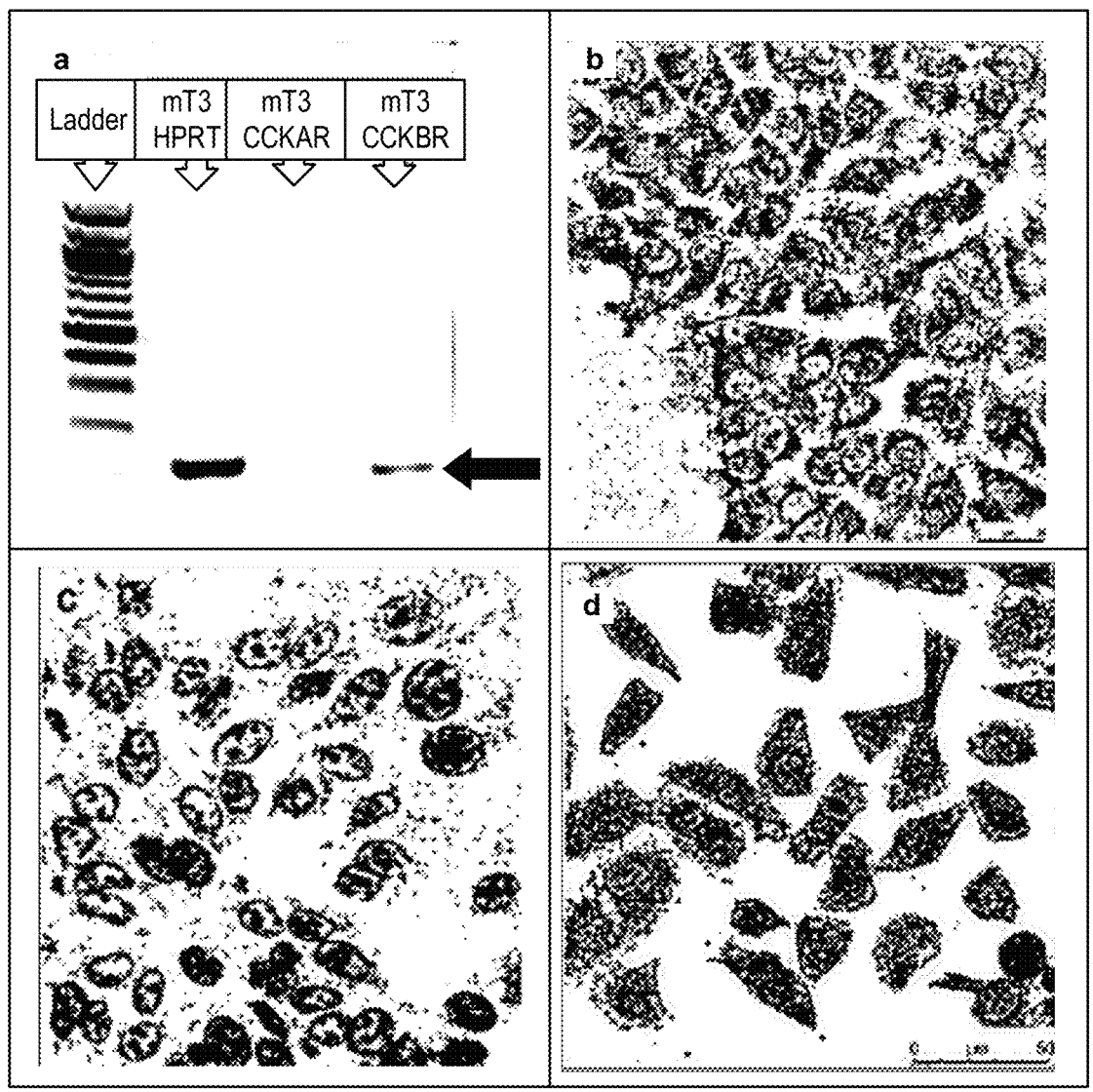
FIGS. 6a-d show characterization of CCK-B receptors on mT3 cells. (a) Gel electrophoresis of RT-PCR products showing that mT3 Murine cancer cells have CCK-B and not CCK-A receptors. HPRT serves as a positive control to confirm integrity of RNA. (b) Immunofluorescence of CCK-B receptor reacted with Dylight 488 CCK-B receptor antibody on mT3 murine cancer cells by confocal microscopy. (c) Hoescht stain demonstrates nucleus of mT3 cells. (d) PANC-1 human pancreatic cancer cells with CCK-B receptors serve as a positive control.

In order to validate the effects of CCKR antagonism and immune checkpoint blockade antibody therapy, an additional study with a PDAC cell line (mT3) in an immunocompetent mouse model was performed. Analysis of the CCKR type in mT3 murine pancreatic cancer cells by RT-PCR showed that mT3 cells expressed CCK-B but not CCK-A receptor mRNA (FIG. 6a). CCK-B receptor protein was confirmed by immunofluorescence (FIG. 6b). Therefore, mT3 cells have characteristics that are representative of human pancreatic cancer, e.g., CCK-B receptor type and mutant KRAS.

Growth of mT3 tumors was significantly slower in mice treated with proglumide or PD-1 antibody monotherapy compared to PBS controls (FIG. 4a). In this experiment, a higher dosing regimen of PD-1 antibody (200 µg every three days) may have resulted in the more pronounced inhibitory effect on tumor size compared to the dose used (125 µg×3 injections) for the Panc02 experiments. Alternatively, the mT3 cancers may be more susceptible to immune checkpoint antibodies. When CCKR blockade was used in combination with the PD-1 antibody, tumor size (FIG. 4a) was significantly decreased. In fact, mice with mT3 pancreatic cancers treated with proglumide or with PD-1 antibody monotherapy survived an average of 12 days longer than PBS control mice. Mice bearing mT3 pancreatic tumors that received the combination of both therapies survived more than 20 days longer than PBS treated controls.

Figure 7:
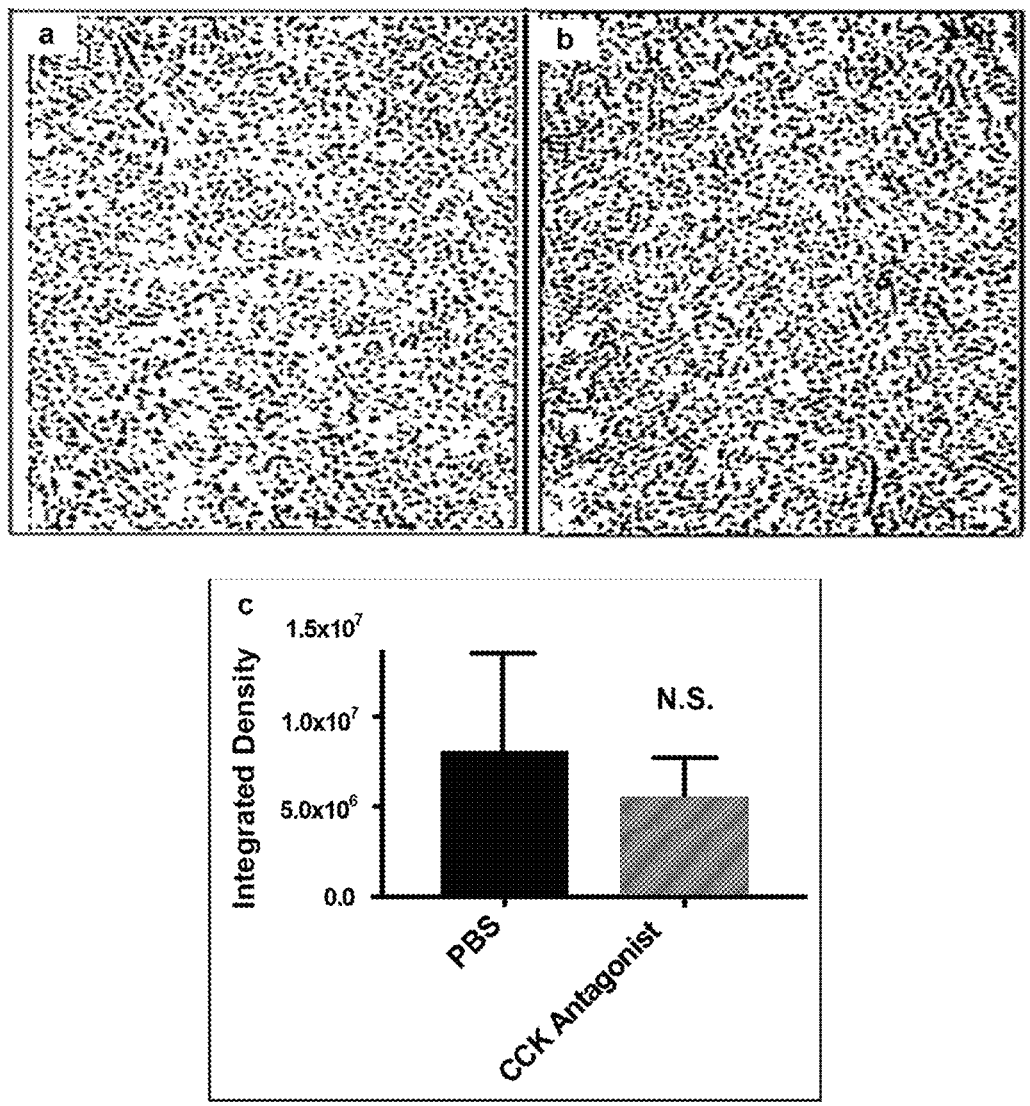
FIGS. 7a-c show α-SMA staining by IHC in mT3 mouse pancreatic cancer tumors. (a) Activated fibroblasts are shown with α-SMA staining in a tumor of a PBS treated mouse. (b) α-SMA staining in a tumor of a mouse treated with proglumide is shown. (c) Densitometry analysis of α-SMA reacted tumors (N=10 each) shows lower α-SMA staining in mice treated with the CCK receptor antagonist but this did not reach significance (p=0.21).

CD4+ TILs (FIG. 4b) and the CD8+ lymphocytes (FIG. 4c) increased significantly in the mice with mT3 tumors and were most pronounced with the combination of the CCKR antagonist and the PD-1 antibody. Likewise, the number of Foxp3+ cells decreased with CCKR antagonism, PD-1 inhibition and combined therapy (FIG. 4d). Fibrosis as demonstrated by Masson's trichrome stain was high in the PBS-treated tumors (FIG. 4e-1) and was noticeably less in mice treated with proglumide (FIG. 4e-2) and in mice treated with the combination therapy (FIG. 4e-4). PD-1 antibody monotherapy did not alter tumor-associated fibrosis (FIG. 4e-3), confirming that the anti-fibrotic effect was a result of CCKR antagonism. Quantitative analysis of the intratumoral fibrosis confirmed that proglumide-treated mice had significantly less fibrosis (p<0.01) than PBS controls and PD-1 monotherapy-treated mice (FIG. 4f). Activated fibroblasts stained positive for α-SMA, and the α-SMA immunoreactivity was somewhat decreased with proglumide, but this change was not statistically significant (FIG. 7) indicating that other fibrosis-associated proteins may be altered by the proglumide.

The studies provide a novel therapeutic approach using CCKR blockade to enhance the response of immunotherapy in pancreatic cancer, a characteristically immune resistant cancer. Since CCKRs have been reported on pancreatic cancer cells, CAFs, and lymphocytes, the studies described herein looked at all three cell types to study the effects of CCKR antagonism in different models of pancreatic carcinogenesis and established pancreatic cancer. In the immune deficient SCID mouse, it was shown that monotherapy with CCKR blockade decreased orthotopic PDAC tumor size and metastases suggesting that some growth inhibitory effects mediated through the CCKR are independent of the immune system and due to prevention of peptide signaling at the cancer epithelial cell. The same dosing schedule was less effective in decreasing primary tumor growth in immune competent mice, but did decrease metastases. These results suggest that CCKR-antagonist monotherapy has anti-tumor and anti-metastatic properties.

Three types of CCK receptors have been characterized and sequenced. The CCK-A receptor is the predominant type found in normal rodent pancreas, whereas the CCK-B receptor variety is the form found in the normal human pancreas. Of interest, when the rodent pancreas undergoes malignant transformation as a result of carcinogen or mutant Kras, the rodent pancreas premalignant or malignant cancer cells can also express the CCK-B receptor type. The third variety of CCK receptor, the CCK-C receptor, is a splice variant of the CCK-B receptor that occurs only in human pancreatic cancer patients with a germline single nucleotide polymorphism (rs1800843). A clinical trial using CCK receptor blockade was attempted many years ago in human subjects with advanced pancreatic cancer, and unfortunately, this trial failed because a selective CCK-A receptor antagonist was used rather than a CCK-B antagonist, the predominant receptor type in human cancer. In this study, two CCK receptor antagonists were used. The L364,718 is a highly potent and selected antagonist to the CCK-A receptor (Chang et al. Characterization of the binding of [3H]-(+/−)-L-364,718: a new potent, nonpeptide cholecystokinin antagonist radioligand selective for peripheral receptors, *Mol Pharmacol* 30:212-7 (1986)), the predominant recent variety in mice. Proglumide (Hahne et al. "Proglumide and benzotript: members of a different class of cholecystokinin receptor antagonists," *Proc Natl Acad Sci USA* 8:6304-8 (1981)) is a weaker nonselective CCK antagonist that has inhibitory properties at both the CCK-A and CCK-B receptor types and is water soluble so it can be easily added to the test animal's drinking water. Because of these properties of CCK receptor antagonists on pancreatic precancerous PanIN progression, cancer growth and the pancreatic tumor-associated fibrosis, this class of pharmaceutical agents could be useful in improving therapy to pancreatic cancer.

As set forth above, combined therapy with a CCKR antagonist and an immune checkpoint antibody changed the number and type of immune cells in the cancer microenvironment. Although both CCKR antagonists can be used to treat pancreatic cancer, some differences in treatment efficacy between the two CCKR antagonists used were observed. A possible explanation for why L364,718 monotherapy was not as effective in inhibiting tumor growth as proglumide may be due to the intermittent administration of L364,718 (three times weekly); proglumide provided a more sustained CCKR blockade since it was administered continuously in the drinking water. Another possible explanation for the greater efficacy of proglumide compared to L364,718 is that proglumide blocks both CCK-A and CCK-B receptors whereas L364,718 blocks just CCK-A receptors. Although Panc02 cells have the CCK-A receptor type, CAFs, pancreatic stellate cells, and lymphocytes have both types of receptors. Therefore, proglumide may have a greater impact on altering the tumor microenvironment to render it more susceptible to immune therapy. Those of skill in the art would know how to select the appropriate antagonist depending in CCK receptor expression in target tissues and/or cells. For human studies where the CCK-B receptor is the predominant receptor type on the cancer epithelial cells, proglumide could also be used as an antagonist, since it has greater activity at the CCK-B receptor. Another potential benefit of using CCKR antagonists in cancer patients is that CCKR blockade may improve pain (Benedetti et al., "The biochemical and neuroendocrine bases of the hyperalgesic nocebo effect," *J. Neurosci.* 26:12014-12022 (2006)). Therefore translating this therapy into clinical practice is possible and may offer new insights to treatment of pancreatic cancer.

In this investigation, it was found that therapy with a low dose of CCK receptor antagonist in addition to an immune checkpoint antibody changed the number and type of immune cells in the pancreatic cancer microenvironment. The dose of the CCK antagonist used in this study (L364, 718; 4 mg/kg, three times weekly (tiw), ip), was previously shown to be an insufficient dose, by itself, to inhibit pancreatic primary tumor growth in an immune competent mouse (Matters et al. Cholecystokinin mediates progression and metastasis of pancreatic cancer associated with dietary fat, *Dig Dis Sci* 59:1180-91 (2014)) but did decrease the number of metastases. In another study, when the dosing regimen was increased to 2 mg/kg twice daily in an immune deficient nude mouse, there was significant reduction in pancreatic cancer tumor size. Likewise, in the current study, it was shown that even using the reduced dosing schedule of three times a week was sufficient to decrease growth of tumors and metastases in SCID mice. These results suggest that CCK-antagonist monotherapy has anti-tumor properties; however, the dose or dosing regimen may need to be increased when used in an immune competent host. Although the dose of the CCK antagonist used alone in this study was insufficient to inhibit primary pancreatic tumor growth alone in the immune competent mouse, the antagonist alone decreased the fibrosis of the tumor microenvironment and the phenotype of the tumor infiltrating lymphocytes. This altered immune state contributed to making the cancer more responsive to immunotherapy.

A variety of treatment strategies have been tried to enhance immune responsiveness of cancers. One approach has been with the use of low-dose cyclophosphamide to decrease the immunosuppressive Tregs. Another recent approach has been the use of toll-like receptor agonists to increase the response to tumor vaccines and immune checkpoint antibodies. In the studies provided herein, it was found that CCKR antagonism and immune checkpoint antibodies also significantly decreased the Tregs, perhaps making the tumors more immune sensitive.

A new finding from this investigation is that the murine cancer cell line, mT3, derived from organoids of the mutant KRAS mouse expresses CCK-B receptors and not CCK-A receptors. Animal models to study cancer progression and therapeutics are essential but these animal models are most useful when they resemble human cancers, particularly with respect to genetics, inflammation, and the immune system in carcinogenesis and therapy. Hence, athymic nude mice bearing human cancer explants are being replaced by genetically modified animal models with intact immune systems. Panc02 cancer cells have traditionally been used to create a syngeneic immune competent murine model of pancreatic cancer. However, unlike human pancreatic cancer, Panc02 cells express wild-type KRAS and CCK-A receptors. Since CCK-B receptors become expressed in the Pdx1-Cre/LSL-Kras$^{G12D}$ mouse under the influence of mutated KRAS, it is not surprising that the mT3 cells derived from this model also express the CCK-B receptors and more closely resemble human pancreatic cancer. These findings could influence cell lines used in future studies in immune competent murine models of PDAC.

Another new discovery from the studies provided herein is that CCKR blockade decreases tumor associated fibrosis that has been proposed to impair therapy (Apte et al., "A starring role for stellate cells in the pancreatic cancer microenvironment," *Gastroenterology* 144:1210-1219 (2013). Proglumide reverses fibrosis by the interference of gastrin or CCK signaling with the CCK receptors on pancreatic stellate cells to prevent activation. As shown herein, CCKR antagonist therapy decreased fibrosis in the pancreas of orthotopic tumors and fibrosis in the mutant KRAS model of carcinogenesis. Pancreatic stellate cells and fibroblasts possess both CCK-A and CCK-B receptor types and complete inhibition of collagen is reported with blockade of both receptors. In the current study, it was shown that CCKR antagonist therapy prevented activation and fibrosis from both pancreatic stellate cells (orthotopic model) and CAFs (subcutaneous tumors). CCKR have also been described on fibroblasts in the periphery (away from the pancreas) and the CCKR antagonist therapy was also effective for tumors remote from the pancreas suggesting that this therapy would be effective for even metastatic lesions or perhaps other cancers associated with extensive fibrosis.

Several methods have been tried to decrease the fibrosis associated with the pancreatic cancer tumor microenvironment in an attempt to improve therapy. Some have tried to decrease tumor associated macrophages by using compounds such as PF-04136309 that blocks CCL2-CCR2 chemokine axis. Investigators are also studying the use of hyaluronidase to decrease tumor associated fibrosis and improve chemotherapy. Unfortunately, many of these methods have systemic toxicity and unlike the approach described herein, these other approaches do not directly attack the tumor epithelial cells, metastatic cells, or recruit effector T-lymphocytes. As a result, these strategies all require secondary chemotherapeutic agents such as gemcitabine to decrease growth of the cancer. Another advantage of using the CCKR as a target for pancreatic cancer treatment is that there are CCKRs located on all three important components of the tumor including the cancer cells, the CAFs, and the immune cells. Given the poor prognosis of advanced pancreatic cancer, novel treatments such as the use of CCKR antagonists should be explored in the clinic In summary, the present studies showed that tumors were larger with more metastases in immune deficient SCID mice compared to orthotopic PDAC tumors of C57BL/6 immune competent mice. Monotherapy with CCKR blockade significantly decreased tumor size and metastases in SCID mice with orthotopic PDAC. Animal survival was significantly prolonged in immune competent mice bearing subcutaneous PDAC xenografts treated with the combination of CCK receptor blockade and immune checkpoint blockade antibodies. Tumor immunohistochemical staining and flow cytometry demonstrated that the tumors of mice treated with the combination regimen demonstrated a significant reduction in Foxp3+ T-regulatory cells and an increase in CD4+ and CD8+ lymphocytes. Trichrome stain analysis revealed at least 50% less fibrosis in mice treated with CCKR antagonist compared to PBS controls. CCKR blockade represents a novel approach to improving survival of PDAC. The mechanism by which this combination therapy improves survival of PDAC could be related to decreasing fibrosis of the tumor microenvironment and changing the signature of the tumor infiltrating lymphocytes. Combining cancer regimens with CCKR blockade could be a new approach to improving survival of patients with advanced PDAC.

What is claimed is:

1. A method for treating a cholecystokinin (CCK) receptor-expressing cancerous tumor in a subject, comprising administering to the subject an effective amount of a CCK receptor inhibitor and an effective amount of an immune checkpoint inhibitor, wherein the CCK receptor inhibitor inhibits one or more CCK receptors selected from the group consisting of a CCK-A receptor, a CCK-B receptor and a CCK-C receptor, and wherein the immune checkpoint inhibitor is a programmed cell death protein 1 (PD1) inhibitor or a cytotoxic T-lymphocyte-associated antigen 4 (CTLA-4) inhibitor.

2. The method of claim 1, wherein the (CCK) receptor-expressing cancerous tumor is a pancreatic tumor.

3. The method of claim 2, wherein the pancreatic tumor is a pancreatic ductal adenocarcinoma.

4. The method of claim 1, wherein the cancerous tumor is resistant to immunotherapy.

5. The method of claim 4, wherein the immunotherapy is treatment with an immune checkpoint inhibitor.

6. The method of claim 1, wherein the tumor expresses one or more CCK receptors selected from the group consisting of a CCK-A receptor, a CCK-B receptor and a CCK-C receptor.

7. The method of claim 1, wherein the CCK receptor inhibitor decreases fibrosis of the tumor.

8. The method of claim 1, wherein the CCK receptor inhibitor selectively inhibits the CCK-A receptor, the CCK-B receptor or the CCK-C receptor.

9. The method of claim 8, wherein the selective CCK-A receptor inhibitor is L364,718.

10. The method of claim 1, wherein the CCK receptor inhibitor inhibits the CCK-A receptor and the CCK-B receptor.

11. The method of claim 10, wherein the CCK receptor inhibitor that inhibits the CCK-A receptor and the CCK-B receptor is proglumide.

12. The method of claim 1, wherein the PD-1 inhibitor is an anti-PD-1 antibody.

13. The method of claim 12, wherein the PD-1-antibody is selected from the group consisting of nivolumab, pembrolizumab and pidilizumab.

14. The method of claim 1, wherein the CTLA-4 inhibitor is an anti-CTLA-4 antibody.

15. The method of claim 14, wherein the anti-CTLA-4 antibody is ipilimumab or tremelimumab.

16. The method of claim 1, further comprising administering one or more chemotherapeutic agents to the subject.

17. The method of claim 16, wherein the one or more chemotherapeutic agents are selected from the group consisting of paclitaxel, gemcitabine, fluorouracil and irinotecan.

18. A method for increasing sensitivity of a (CCK) receptor-expressing cancerous tumor in a subject to immunotherapy, the method comprising administering to the subject an effective amount of a CCK receptor inhibitor prior to administering to the subject an immunotherapy, wherein the CCK receptor inhibitor inhibits one or more CCK receptors selected from the group consisting of a CCK-A receptor, a CCK-B receptor and a CCK-C receptor, and wherein the immunotherapy is a programmed cell death protein 1 (PD1) inhibitor or a cytotoxic T-lymphocyte-associated antigen 4 (CTLA-4) inhibitor.

19. The method of claim 18, wherein the (CCK) receptor-expressing cancerous tumor is a pancreatic tumor.

20. The method of claim 19, wherein the pancreatic tumor is a pancreatic ductal adenocarcinoma.

21. The method of claim 18, wherein the cancerous tumor is resistant to immunotherapy.

22. The method of claim 21, wherein the immunotherapy is treatment with an immune checkpoint inhibitor.

23. The method of claim 18, wherein the CCK receptor inhibitor decreases fibrosis of the tumor.

24. The method of claim 18, wherein the CCK receptor inhibitor inhibits one or more CCK receptors selected from the group consisting of a CCK-A receptor, a CCK-B receptor and a CCK-C receptor.

25. The method of claim 24, wherein the CCK receptor inhibitor selectively inhibits the CCK-A receptor, the CCK-B receptor or the CCK-C receptor.

26. The method of claim 25, wherein the selective CCK-A receptor inhibitor is L364,718.

27. The method of claim 24, wherein the CCK receptor inhibitor inhibits the CCK-A receptor and the CCK-B receptor.

28. The method of claim 27, wherein the the CCK receptor inhibitor that inhibits the CCK-A receptor and the CCK-B receptor is proglumide.

29. A method for treating a cholecystokinin (CCK) receptor-expressing cancerous tumor in a subject, comprising administering to the subject an effective amount of a CCK receptor inhibitor and an effective amount of an immune checkpoint inhibitor, wherein the CCK receptor inhibitor is selected from the group consisting of L364,718 and proglumide, and wherein the immune checkpoint inhibitor is selected from the group consisting of nivolumab and ipilimumab.

* * * * *

SEQUENCE LISTING

<160> NUMBER OF SEQ ID NOS: 6

<210> SEQ ID NO 1
<211> LENGTH: 21
<212> TYPE: DNA
<213> ORGANISM: Artificial sequence
<220> FEATURE:
<223> OTHER INFORMATION: Synthetic construct

<400> SEQUENCE: 1
cttttctgcc tggatcaacc t                                          21

<210> SEQ ID NO 2
<211> LENGTH: 21
<212> TYPE: DNA
<213> ORGANISM: Artificial sequence
<220> FEATURE:
<223> OTHER INFORMATION: Synthetic construct

<400> SEQUENCE: 2
accgtgataa ccagcgtgtt c                                          21

<210> SEQ ID NO 3
<211> LENGTH: 20
<212> TYPE: DNA
<213> ORGANISM: Artificial sequence
<220> FEATURE:
<223> OTHER INFORMATION: Synthetic construct

<400> SEQUENCE: 3
gatggctgct acgtgcaact                                            20

<210> SEQ ID NO 4
<211> LENGTH: 19
<212> TYPE: DNA
<213> ORGANISM: Artificial sequence
<220> FEATURE:
<223> OTHER INFORMATION: Synthetic construct

<400> SEQUENCE: 4
cgcaccaccc gcttcttag                                             19

<210> SEQ ID NO 5
<211> LENGTH: 18
<212> TYPE: DNA
<213> ORGANISM: Artificial sequence
<220> FEATURE:
<223> OTHER INFORMATION: Synthetic construct

<400> SEQUENCE: 5
tcctcctcag accgcttt                                              18

<210> SEQ ID NO 6
<211> LENGTH: 23
<212> TYPE: DNA
<213> ORGANISM: Artificial sequence
<220> FEATURE:
<223> OTHER INFORMATION: Synthetic construct

<400> SEQUENCE: 6
ttttccaaat cctcggcata atg                                        23